(12) United States Patent
Shaffer et al.

(10) Patent No.: US 9,134,242 B2
(45) Date of Patent: Sep. 15, 2015

(54) METHOD AND APPARATUS FOR RETRIEVAL OF AMPLITUDE AND PHASE OF NONLINEAR ELECTROMAGNETIC WAVES

(75) Inventors: Etienne Shaffer, Lausanne (CH); Christian Depeursinge, Préverenges (CH)

(73) Assignee: ECOLE POLYTECHNIQUE FEDERALE DE LAUSANNE (EPFL), Lausanne (CH)

(*) Notice: Subject to any disclaimer, the term of this patent is extended or adjusted under 35 U.S.C. 154(b) by 332 days.

(21) Appl. No.: 13/266,319

(22) PCT Filed: Apr. 23, 2010

(86) PCT No.: PCT/IB2010/051787
§ 371 (c)(1),
(2), (4) Date: Nov. 28, 2011

(87) PCT Pub. No.: WO2010/125508
PCT Pub. Date: Nov. 4, 2010

(65) Prior Publication Data
US 2012/0069345 A1    Mar. 22, 2012

(30) Foreign Application Priority Data

Apr. 27, 2009  (WO) .................. PCT/IB2009/051716

(51) Int. Cl.
*G01B 9/021*    (2006.01)
*G01N 21/64*    (2006.01)
(Continued)

(52) U.S. Cl.
CPC .......... *G01N 21/6458* (2013.01); *G01B 11/002* (2013.01); *G01B 11/2441* (2013.01); *G02B 21/086* (2013.01); *G02B 21/14* (2013.01)

(58) Field of Classification Search
CPC ............... G01B 9/021–9/029; G01B 9/02097; G01B 11/24; G01B 11/2441; G01N 21/453; G01M 11/331

USPC .................................. 356/450–521; 382/154
See application file for complete search history.

(56) References Cited

U.S. PATENT DOCUMENTS 7,529,533 B2 * 5/2009 Bellantoni .................... 455/334
2005/0280827 A1  12/2005 Potma et al.
(Continued)

FOREIGN PATENT DOCUMENTS

EP              1 541 992        6/2005
WO       WO 2008/127432       10/2008
WO       WO 2008/156776       12/2008

OTHER PUBLICATIONS

International Search Report for PCT/IB2010/051787, mailed Sep. 22, 2010.
Written Opinion of the International Searching Authority for PCT/IB2010/051787, mailed Sep. 22, 2010.
(Continued)

*Primary Examiner* — Michael A Lyons
*Assistant Examiner* — Hina F Ayub
(74) *Attorney, Agent, or Firm* — Nixon & Vanderhye, PC

(57) ABSTRACT

The present invention discloses a method and its associated apparatus to retrieve the amplitude and, especially, the phase of nonlinear electromagnetic waves. The application field of the present invention is optical imaging. A sample is probed by coherent electromagnetic radiation, and by a nonlinear interaction such as harmonic generation a nonlinear object wave is emitted. A nonlinear reference wave is generated by interaction of the same nature with the coherent electromagnetic radiation, and an interference between the nonlinear object wave and the nonlinear reference wave is sensed by a detector array. As an example, the technique makes possible real-time nanometric localization and tracking of nonlinear field emitters, such as, but not limited to, nanoparticles.

10 Claims, 7 Drawing Sheets

(51) Int. Cl.
*G01B 11/00* (2006.01)
*G01B 11/24* (2006.01)
*G02B 21/08* (2006.01)
*G02B 21/14* (2006.01)

(56) References Cited

U.S. PATENT DOCUMENTS

2006/0033930 A1* 2/2006 Misawa et al. ............... 356/491
2010/0165348 A1* 7/2010 Fleischer et al. ............. 356/458
2011/0019179 A1* 1/2011 Molin et al. .................. 356/32

OTHER PUBLICATIONS

Chia-Lung, H. et al., "Three-dimensional harmonic holographic microcopy using nanoparticles as probes for cell imaging", Optics Express, vol. 17, No. 4, (Feb. 11, 2009), pp. 2880-2891.
Pu, Y. et al., "Harmonic holography: a new holographic principle", Applied Optics, vol. 47, No. 4, (Feb. 1, 2008), pp. A103-A110.
Wikipedia: "Nonlinear optics" Internet Citation, (Sep. 6, 2010), pp. 1-8.
Schnars, U., "Direct phase determination in hologram interferometry with use of digitally recorded holograms", Journal of the Optical Society of America, vol. 11, No. 7, (Jul. 1, 1994), pp. 2011-2015.

* cited by examiner

US 9,134,242 B2

METHOD AND APPARATUS FOR RETRIEVAL OF AMPLITUDE AND PHASE OF NONLINEAR ELECTROMAGNETIC WAVES

This application is the U.S. national phase of International Application No. PCT/IB2012/051787, filed 23 Apr. 2010, which designated the U.S., and claims priority to IB Application No. PCT/IB2009/051716, filed 27 Apr. 2009, the entire contents of each of which are hereby incorporated by reference.

FIELD OF THE INVENTION

The present invention relates to methods and associated apparatuses which generate nonlinear electromagnetic waves.

BACKGROUND OF THE INVENTION

Microscopy is an essential tool that is driving progress in cell biology, and is still the only practical means of obtaining spatial and temporal resolution for living cells and tissues observation. Microscopy involves electromagnetic radiation transmitted through or reflected from the sample through a single or multiple lens element(s) to allow a magnified view of the sample. The resulting image can be detected directly by the eye, imaged on a photographic plate or captured digitally.

Over the centuries, optical microscopy has addressed the need to see what happens at the microscopic level. As the needs evolved, so did microscopy. This way, higher magnification objectives and aberration-corrected objectives respectively answered the need to produce larger images and images of higher quality, while better resolved objectives and shorter wavelength sources answered the need to see and distinguish smaller and smaller elements.

But as the investigated objects became more and more complex, the need to have better and even material-specific contrast arose. Fluorescence, phase contrast and nonlinear microscopy were thus developed.

Fluorescence Microscopy

The most commonly encountered solution for material-specific contrast is fluorescence microscopy. Fluorescence is the emission of electromagnetic radiation by a substance that has beforehand absorbed electromagnetic radiation of a different wavelength. In fluorescence microscopy, the electromagnetic radiation resulting from fluorescence is separated from the excitation by some technical mean, and contributes alone to the image formation.

The fluorescent substance can be the material of interest, but most generally it consists in a marker, called fluorophore, biochemically functionalized to bind to the material of interest. Using such exogenous marker is referred to as staining and is not always ideal, as the marker can affect the object and alter its behavior or characteristics. Fluorophores can even be toxic to the object of interest. Although exogenous labels are generally applicable to any animal model and benefit from decades of acceptance in the laboratory, there has been a recent trend toward imaging with genetically encoded markers, mostly green fluorescent proteins (GFPs) or their variants. Because they can be encoded in DNA, these endogenous genetic markers can be globally targeted to well-defined regions in intact animals.

Unfortunately, fluorophores lose their ability to fluoresce as they are illuminated in a process called photobleaching. Special care must be taken to prevent photobleaching through the use of more robust fluorophores, by minimizing illumination, or by introducing a scavenger system to reduce the rate of photobleaching.

Phase-contrast Imaging

In phase contrast microscopy, small phase shifts in the light passing through a transparent object are converted into amplitude or contrast changes in the image. A phase contrast microscope does not require staining to view the slide. Nowadays, there exist many techniques for phase-contrast imaging.

Among the most interesting are the techniques—often based on interferometric (or holographic) principles—that provide quantitative phase imaging. These techniques literally added a new dimension to microscopy by making possible nanometer-scale surface measurements, and very precise refractive index tomography. Digital holographic microscopy (DHM) is one of such techniques [E. Cuche, P. Marquet and C. Depeursinge, "Simultaneous amplitude-contrast and quantitative phase-contrast microscopy by numerical reconstruction of Fresnel off-axis holograms," Applied Optics, 38. p. 6994-7001 (1999)].

Nonlinear Microscopy

Nonlinear optics is a relatively new trend in microscopy. The main idea of this technique is to exploit the nonlinear responses of the polarization of material to electric field to generate nonlinear radiations that will form images. The differences between the nonlinear responses of different materials provide a highly specific contrast.

As the probability for nonlinear processes to occur is very low, the excitation electromagnetic source, generally a femtosecond laser, is tightly focused in the object. As a consequence, background signal is strongly suppressed, since the probability that multiphoton processes occur outside the focus volume of the excitation beam is negligible.

Furthermore, as the generated signal generally lies in the visible or near-infrared region of the electromagnetic spectrum, the excitation source is generally a near-infrared radiation. Near-infrared radiation is much less absorbed and scattered by biological tissues and makes possible deep tissue imaging. In addition, these lower-energy photons are less likely to cause damage outside the focal volume.

Nonlinear microscopy generally uses a scanning, confocal-type microscope. Because they require scanning of the illumination or the object, such microscopes are intrinsically slow and vulnerable to vibrations.

Nonlinear microscopy can be divided in two distinct categories: incoherent and coherent nonlinear microscopy.

Incoherent Nonlinear Microscopy

Incoherent nonlinear microscopy produces signals whose phase is random and whose power is proportional to the concentration of radiating molecules.

Multiphoton fluorescence microscopy, a fluorescence imaging technique that allows imaging of living tissue up to a much higher depths [W. Denk, and K. Svoboda, "Photon upmanship: Why multiphoton imaging is more than a gimmick," Neuron, 18. p. 351-357 (1997)], is an example of incoherent nonlinear microscopy. Multiphoton fluorescence microscopy requires multiple photons to be absorbed simultaneously to provide enough energy to generate free charge carriers in the material. This special case differentiates from the above-mentioned fluorescence microscopy by having emitted EM radiation with a shorter wavelength (and higher energy) than the absorbed EM radiation and requiring multiple excitation photons to be absorbed simultaneously.

Even though some materials have intrinsic fluorescence properties, multiphoton fluorescent microscopy relies on markers, or fluorophores, to provide image contrast.

Coherent Nonlinear Microscopy

Coherent nonlinear microscopy relies on signals whose phase is rigorously prescribed by a variety of factors, including the excitation light phase and the geometric distribution of the radiating molecules. Coherent signal power is proportional to the concentration of radiating molecules squared. Nonlinear coherent microscopy is based on the simultaneous scattering of two or more photons. Its main advantage over fluorescence lies in the fact that nonlinear interactions occur instantaneously and theoretically make possible ultrafast measurements.

Harmonic generation, coherent anti-Stokes Raman scattering, sum- and difference-frequency generation are examples of coherent nonlinear microscopy.

Nonlinear microscopy can rely on markers to provide contrast, but does not exclusively require so. Indeed, most materials have intrinsic nonlinear response of some sort, or lack of, which provide contrast to nonlinear microscopy. Using intrinsic nonlinear properties of materials reduces the amount of time and efforts for sample preparation and avoids its contamination by possibly toxic, or chemically active, markers. Nevertheless, contrast agents can still be used for their nonlinear responses and high selectivity, especially when functionalized, or bioconjugated. One example is the use of styryl dye derivatives as an effective Second Harmonic Generator (SHG) sensor of membrane potential [A. C. Millard, L. Jin, M.-D. Wei, J. P. Wuskell, A. Lewis, L. M. Loew, "Sensitivity of second harmonic generation from styryl dyes to transmembrane potential," Biophys J 86. p. 1169-1176 (2004)]. It is an emerging trend to develop markers specifically for coherent nonlinear microscopy applications [C. L. Hsieh, R. Grange, Y. Pu and D. Psaltis, "Bioconjugation of barium titanate nanocrystals with immunoglobulin G antibody for second harmonic radiation imaging probes," Biomaterials 31. p. 2272-2277 (2010), J. Extermann, L. Bonacina, E. Cuna, C. Kasparian, Y. Mugnier, T. Feurer and J. P. Wolf, "Nanodoublers as deep imaging markers for multi-photon microscopy," Optics Express 17. p. 15342-15349 (2009).]. A large variety of nanocrystals, among which are BaTiO3. ZnO, KTiOPO4 (KTP), Fe(IO3)3 and KNbO3. were thus developed for harmonic generation imaging.

Gold nanoparticles are especially promising as nonlinear markers for biological. First, they are totally biocompatible, chemically inert and non-toxic. In addition, a vast knowledge of surface chemistry of noble metals has already been acquired, which makes their functionalization, or bioconjugation, relatively easy. Finally, resonance effects, such as surface plasmon resonance, provide tremendous signal enhancement factors.

Nonlinear Holography

Nonlinear holography, an emerging microscopy technique, consist in exploiting the coherent nature of nonlinear interactions to record the interference between the nonlinear wave generated by the object and a nonlinear reference wave of the same nature.

Intensity images are obtained from processing of the recorded interference patterns, and a single hologram contains all the information for a 3D tomography of the nonlinear EM wave intensity. A direct consequence of this is that nonlinear holography requires no scanning of any sort. In particular, it makes nonlinear holography vibration-insensitive.

Nonlinear harmonic holography [PCT applic.number PCT/US07/85409] has been described as a technique and system that combines holography and the nonlinear interaction named second harmonic generation, and that enables holographic recording of 3D intensity images with femtosecond framing time.

Nonlinear Phase-contrast Imaging

Just as phase imaging added a new dimension to classical (or linear) optical microscopy, nonlinear phase imaging is expected to provide additional information, inaccessible to state of the art nonlinear imaging techniques, and thus open a large panel of new applications. Microscopy techniques capable of recovering the phase of nonlinear electromagnetic waves will become of great interest.

OBJECTIVE OF THE INVENTION

The objective of this invention is to provide a method and the related apparatus for retrieval of the phase of nonlinearly generated electromagnetic waves, further abbreviated by nonlinear EM waves.

The phase of a nonlinear EM wave provides very precise information on the space/time coordinates of where it was generated.

In particular, the retrieval of the phase of nonlinear EM waves makes possible localization of NL emitters at nanometer-scale resolution. Nanometric 3D-tracking of nanoparticles and instantaneous tomographic images of cell membranes or components are application examples directly resulting from the retrieval of the phase of nonlinear EM waves.

In addition, energy and/or matter flux can be detected by changes in the phase of the nonlinear EM wave.

In particular, temporal monitoring of the NL phase makes possible the detection of dielectric or morphological changes in the NL emitter or in its vicinity.

SUMMARY OF THE INVENTION

Disclosed in this invention are an original method and the associated apparatus to determine, by retrieval and processing of the phase of a nonlinear EM wave, the space/time coordinates where the nonlinear interaction occurred. Examples of such nonlinear electromagnetic waves include, but do not limit to, electromagnetic waves resulting from harmonic generation. The same approach can be claimed for any other nonlinear processes such as sum or difference frequency wave generation, and multi-wave generation such as Coherent Anti-Stokes Raman Scattering (CARS).

Also disclosed in this invention are an original method and the associated apparatus to detect and monitor, by retrieval and processing of the phase of a nonlinear EM wave, flux of energy and/or matter.

In particular, the technique makes possible real-time nanometric localization and tracking of nonlinear field emitters, such as, but not limited to, nanoparticles.

In particular, access the phase of a nonlinear EM wave provides information on the nature and state of the matter with which the source electromagnetic wave interacted with.

In particular, energy and/or matter flux can be detected as they result in changes of the phase of the nonlinear EM waves.

DETAILED DESCRIPTION OF THE INVENTION

Figure 1:
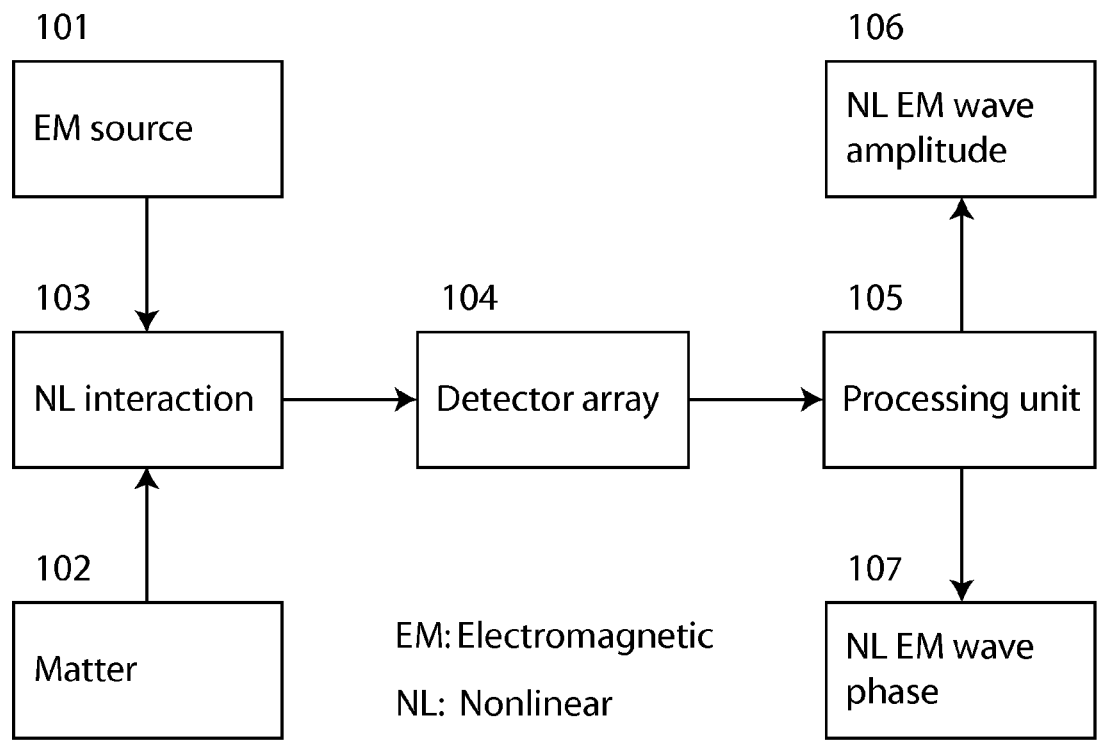
FIG. 1 is a block schematic describing the general process for retrieval of the amplitude and the phase of a nonlinear electromagnetic (EM) wave.

Fundamental Concepts
Electromagnetic Field

An electromagnetic field is a physical field produced by electrically charged objects and consisting in a combination of an electric field, produced by stationary charges, and a magnetic field, produced by moving charges (currents). The electromagnetic field extends indefinitely throughout space and time and describes the electromagnetic interaction that is, just like gravitation, weak interaction, and strong interaction, one of the four fundamental forces of nature.

Electromagnetic Wave

An electromagnetic wave (EM wave) is an electromagnetic disturbance that propagates through space and time and that can involve energy transfer. A propagating electromagnetic wave is generally defined by its speed, its direction, its oscillation frequency, its amplitude and its phase.

Medium

A medium, sometimes referred to as an optical medium, is the environment in which an electromagnetic wave propagates. A medium generally consist of matter (solid, liquid, gas), but can also consist in an absence of matter (vacuum). Medium are sensitive to electromagnetic fields, and the presence of electromagnetic waves will induce charge dipoles in a medium. The dielectric polarization is the vector field that expresses the density of permanent or induced electric dipole moments in a dielectric material.

Light-matter Interactions

Matter and electromagnetic waves affect one another through the fundamental forces of nature. Through these interactions, matter can, among other things, emit, absorb, bend and slow electromagnetic waves. Light-matter interactions can be divided in two categories: linear and nonlinear interactions.

A. Linear Interactions: Light-matter interactions are said to be linear when the dielectric polarization of a medium responds linearly to the electric field of electromagnetic waves. Refraction is an example of a linear light-matter interaction.

B. Nonlinear Interactions: Light-matter interactions are said to be nonlinear when the dielectric polarization of a medium does not respond linearly to the electric field of electromagnetic waves. Nonlinear interactions can be classified with regards to the power of the electric field with which the dielectric polarization of the medium responds. Second harmonic generation is an example of second order nonlinear light-matter interaction.

Nonlinear Electromagnetic Waves

Nonlinear electromagnetic wave refers to the electromagnetic wave resulting from the nonlinear interaction of electromagnetic wave(s) with some medium.

Phase Retrieval of Nonlinear Electromagnetic Waves

Similarly to classical electromagnetic waves, non-linear waves are characterized by a phase describing, in angle, the position of its oscillation within one period, at a given time and position. The phase of electromagnetic and, in particular, nonlinear electromagnetic waves is highly sensitive to spatial and temporal parameters describing the interaction of the waves and provide therefore highly valuable information about the probed samples. However, measuring the phase of a wave is a complex task in the electromagnetic field, as a result of the very high frequency and very short wavelength of the radiations.

Phase retrieval is commonly used to designate methods and devices adapted to measure, to probe or to monitor the phase of a wave, and apply here specifically to the measurement, the probing, or the monitoring of the phase of a nonlinear electromagnetic wave.

The Object and the Object Wave

The object refers to the investigated material of interest, probed by use of an electromagnetic wave, and will be sometime called sample or specimen. On a general note, a physical object is a collection of masses, taken to be one. In other words, the object can be considered as a piece of matter.

For the present invention, it is important to note that the object comprises elements generating a nonlinear interaction. Therefore, the object wave, which designates the wave resulting from the interaction between the object and the electromagnetic wave, comprises a non-linear component, sometimes called a nonlinear object wave.

Disclosed in this invention are an original method and the associated apparatus to provide a measurement of the amplitude and, especially, the phase of electromagnetic waves resulting from a nonlinear process. An essential feature of the invention is the retrieval of the phase of the nonlinear electromagnetic wave.

FIG. 1 presents a block diagram describing the principle of this invention in its more general form. An electromagnetic source (101) interacts with matter (102). This interaction is a nonlinear (NL) interaction (103), which results in the emission of a nonlinear EM wave. A combination of a detector array (104) and a processing unit (105) makes possible the retrieval of the amplitude (106) and, more importantly, the phase (107) of the nonlinear EM wave.

The Source (101)

The apparatus comprises at least one electromagnetic radiation source (101) of coherent nature. In particular, the source can be a laser. Pulsed lasers with sub-nanosecond pulses are generally preferred, since they provide very high peak powers and thus generate stronger nonlinear interactions. Continuous-wave lasers, as well as any kind of electromagnetic radiation sources, could also be used, as long as the nonlinear EM radiation resulting from the nonlinear interaction (103) can be detected by the detector (104).

The Matter (102)

The apparatus comprises at least one sample comprising at least one element called matter (102) having at least one non-zero high order polarization response to electric fields for nonlinear interaction (103) with the EM radiation source (101). In particular, the matter (102) can be intrinsically comprised into the investigated object. In particular, the matter (102) can be a marker, such as a nanoparticle or a fluorophore. In particular, the matter (102) can be a material in the vicinity of the investigated object.

The Nonlinear Interaction (103)

The principle requires a nonlinear interaction (103) to generate a nonlinear EM radiation. In particular, the nonlinear interaction (103) can be harmonic generation. In particular, the nonlinear interaction (103) can be sum- or difference-frequency generation. In particular, the nonlinear interaction (103) can be multiple-wave mixing, e.g. Coherent Anti-Stokes Raman Scattering (CARS). In particular, the nonlinear interaction (103) can be generation of a so-called white-light continuum.

Detector Array (104) and Processing Unit (105)

The apparatus comprises at least one detector array (104) sensitive to electromagnetic radiations, and a processing unit (105). The processing unit (105) can be built-in the detector array (104), or the detector array (104) and the processing unit (105) can be separated entities. In a preferred embodiment of the present invention, the detector array (104) comprises a camera, such as a video camera, a CCD camera, or a CMOS camera, and the processing unit (105) comprises a computer.

The detector array (104) records the nonlinear EM radiation resulting from the nonlinear interaction (103) and the processing unit (105), processes the signals detected by the detector array in order to provide the phase of the nonlinear (NL) electromagnetic (EM) wave (107) and the amplitude of the nonlinear (NL) electromagnetic (EM) wave (106). Equivalently the intensity of the nonlinear electromagnetic wave can be provided instead of its amplitude.

Figure 2:
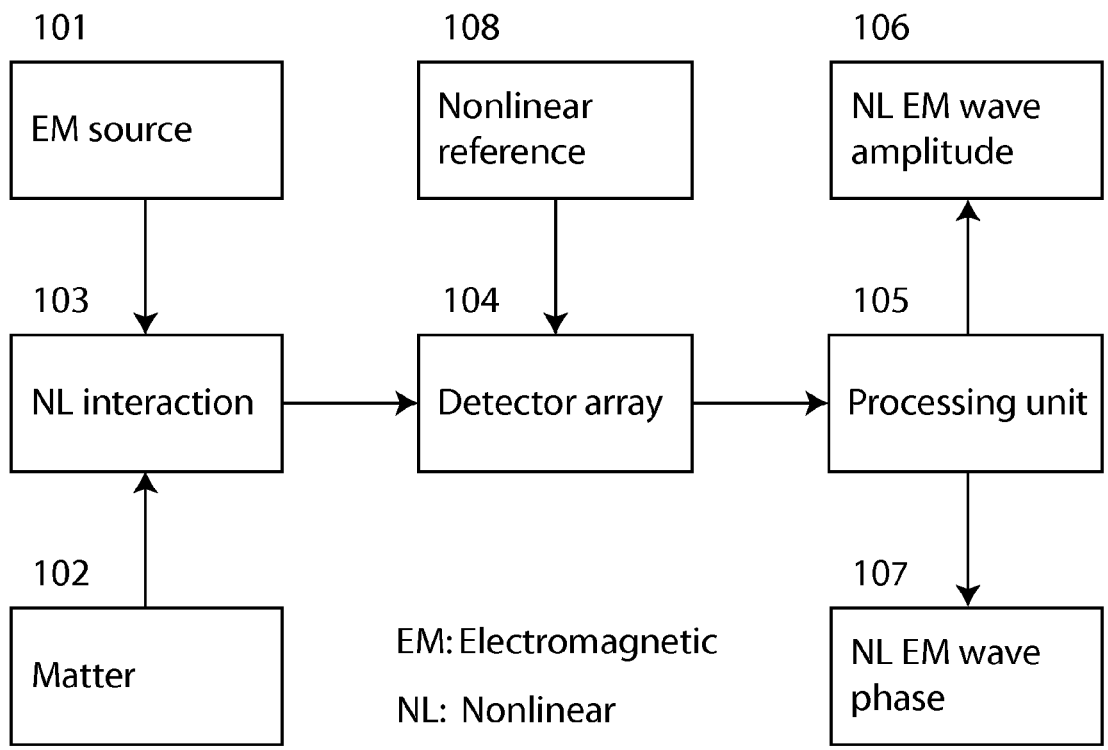
FIG. 2 is a block schematic describing the general process for retrieval of the amplitude and the phase of a nonlinear EM wave, for the specific case that makes use of a nonlinear reference to encode the amplitude and phase of the nonlinear EM wave on a detector array.

In one embodiment presented in FIG. 2, apparatus and methods according to the present invention may use a nonlinear reference wave (107), recorded simultaneously with the non-linear wave resulting from the non-linear interaction (103). Such type of configurations enables phase recording by use of an interference process as commonly used in classical interferometry or holography, except that this interference occurs between non-linear waves with the present invention.

Apparatus and methods according to the present invention, in a scheme with (FIG. 2) or without (FIG. 1) nonlinear reference (107), and assuming adaptations for nonlinear electromagnetic waves, may use diverse devices permitting to measure the phase of an electromagnetic wave. Among such devices, we can mention those using the principles of: wavefront sensing, Hartmann-Shack wavefront sensing, interferometry, interference microscopy, shearing interferometry, lateral shearing interferometry, 4-wave lateral shearing interferometry, phase-shifting interferometry, holography, digital or numerical holography, digital holographic microscopy, quantitative phase imaging, quantitative phase microscopy, phase reconstruction by use of the transport of intensity equation, Fourier phase microscopy, Hilbert phase microscopy, Diffraction Phase Microscopy or tomography, heterodyne Mach-Zehnder phase microscopy.

The Nonlinear Reference (108)

Among devices able to measure the phase of a radiation, those based on interferometry or holography are of particular interest for implementing the present invention. In interferometry or holography, two mutually coherent waves interfere to create an interferogram or a hologram. A first wave called, object wave interact with the sample, and a second wave called reference wave is issued from the same source. Here the formalism is equivalent, except that the object wave is a nonlinear object wave generated by a nonlinear interaction (103) in the sample, and except that the reference wave has to be a non-linear reference wave (107) to interfere with the nonlinear object wave. Three basic approaches exist for the generation of the nonlinear reference (108):

Self-Reference Approach: The nonlinear object wave interferes with itself. The detector records the interferogram resulting from self-interference. Shearing interferometry techniques are examples of self-reference generated interferences.

Local Reference Approach: The nonlinear reference wave (107) is generated by nonlinear interaction of the EM source with the environment of the sample. The reference wave is said to be local, since it is generated in the vicinity of the object and since it travels along the object wave. The detector array (104) records the hologram resulting from their mutual interference.

External Reference Approach: The reference wave is generated by nonlinear interaction of the EM source (101) with a material separated from the sample. In this approach, the reference is said to be external, since it is not generated in the vicinity of the object. The object wave and the reference wave are recombined by beam shaping elements and the detector array records the hologram resulting from their mutual interference.

Many methods exist to retrieve the phase from interferograms or holograms and could be use with the proposed apparatus. Depending on the approach and on the incidence angle the reference wave makes with the object wave on the detector array, in-line or off-axis configurations can be used with the proposed apparatus. If in-line is used, phase shifting interferometry techniques can be used to filter out the square terms or mutual coherence terms. Otherwise the filtering can be done in the spatial frequency domain.

Nonlinear Digital Holographic Microscopy

The present invention can be implemented on a wide variety of devices for wavefront analysis providing the phase an electromagnetic wave with minor adaptations for handling nonlinear waves. A particular case is presented in FIG. 3 which presents the schematic view of an instrument according to the present invention, adapted from the general design of a transmission holographic microscope. A first beam splitter divides the EM radiation of the source wave into two parts: A first part is reflected towards a condenser lens and directed to the specimen, a second part is directed to a non-linear crystal. The nonlinear object wave (O) is generated by nonlinear interaction in the sample and collected by a microscope objective and a tube lens to form a magnified image directed towards the detector array. The nonlinear reference wave (R) is generated by use of a nonlinear crystal located in the so-called reference arm. A second beam splitter recombines the nonlinear object and reference waves, which interfere on the detector array to form a hologram. Between the second beam splitter and the detector array, a band-pass filter is introduced to suppress the portions of the initial electromagnetic radiation that have not been modified by a non-linear interaction. As presented inset the off-axis configuration, with nonlinear object and reference waves reaching the detector array with an angle θ between their directions of propagation, is of particular interest since it enables to record the phase information with a single hologram acquisition.

Figure 3:
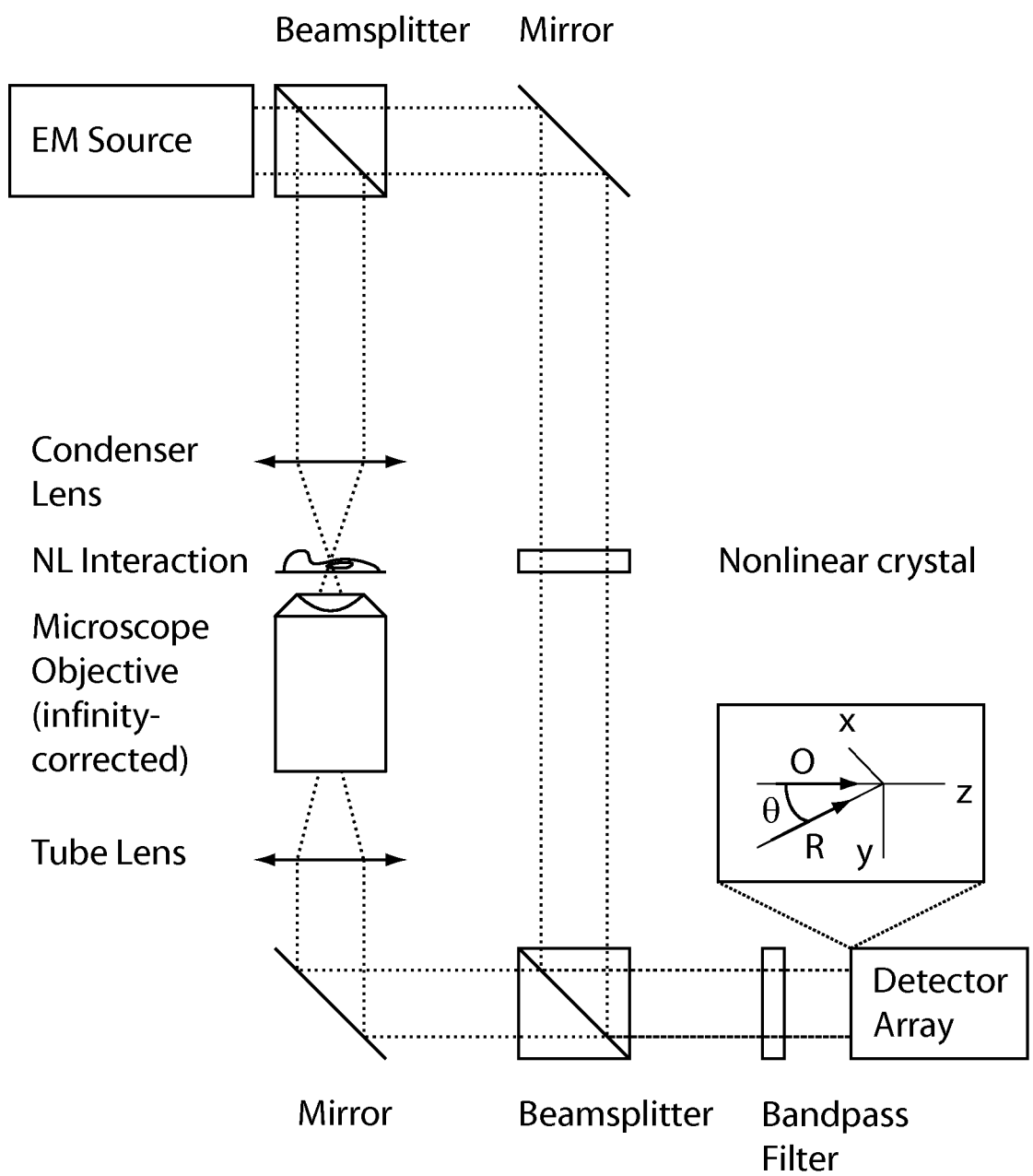
FIG. 3 illustrates a possible implementation of the apparatus, for the specific case where the nonlinear interaction is second harmonic generation, and where a nonlinear EM reference wave generated by a nonlinear crystal is used to encode the amplitude and phase of the nonlinear object wave on a detector array.

The setup of FIG. 3 gives a practical example of realization of an apparatus according to the present invention. For phase reconstruction from holograms acquired with this configuration, diverse processing methods can be applied such as those described by Colomb et al. in U.S. Pat. No. 7,649,160. wave front sensing method and apparatus.

Out of Focus Recording

In addition, it is important to point out that digital holographic methods, as described by the apparatus of FIG. 3, generally record the hologram in an out-of-focus configuration with a magnified image located behind the camera, or in front of the camera, at a certain distance from the detector plane. Such configurations are of particular interest for detecting the phase of nonlinear waves emitted by markers and nano-particles in particular. Indeed, for such objects, potentially smaller than the resolution of microscope objectives, in-focus images concentrates the signal at the pixel level, or even sub-pixel level, making difficult to extract reliable phase measurements. With an out-of focus configuration, the phase response of particles is spread over a larger area that is better adapted to extract a phase signal.

Contrary, the intensity or the amplitude of a nonlinear wave is better to be exploited in focus since it is in this case that it brings the highest accuracy for estimating the position of a nonlinear emitter. Thanks to its capability of numerical focusing, which enables to translate very easily and rapidly the plane of image reconstruction from in-focus to out-of focus and vice versa, digital holographic microscopy (DHM) offers particularly attractive possibilities for the implementation of the present invention. In particular, the combination of intensity-based in focus reconstruction, with phase-based out-of-focus reconstruction, enables three-dimensional tomographic imaging with an improved resolution, especially in the axial direction.

Space/Time Coordinates of the Nonlinear Generation

Figure 4:
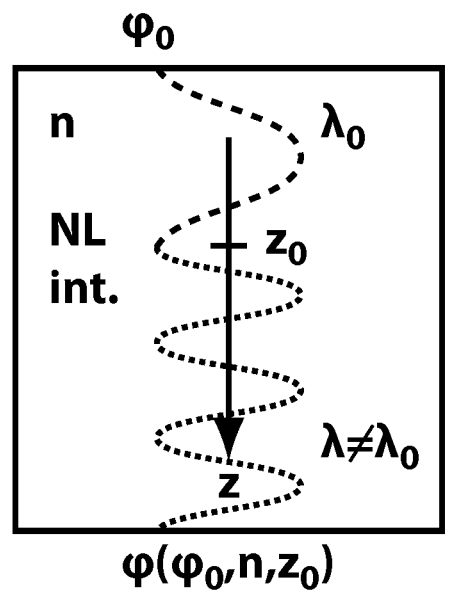
FIG. 4 illustrates how the phase of the nonlinear EM wave depends on the position where the nonlinear interaction occurred.

By retrieving the amplitude and phase, or phase only, of a nonlinear EM wave, the apparatus and method according to the present invention can be used to provide information on the space, time or space-time coordinates at which was generated the nonlinear EM wave. Basically, the measurement principle applies to coherent nonlinear interactions that produce EM waves with wavelengths different from that of the EM source wave and is illustrated in FIG. 4. In this case, the observed phase of a nonlinear EM wave depends on:
  the phase value of the EM source wave at the coordinates of nonlinear interaction;
  the optical path length, which, in turn, depends on the refractive indices of all encountered media and on the coordinates of the source, the nonlinear interaction and the detector.

As a direct consequence, the observed phase of a nonlinear EM wave provides information on the position at which the nonlinear interaction occurred.

As presented in FIG. 4, the simple fact that a nonlinear interaction modifies the wavelength of the initial radiation means automatically that the phase of the non-linear radiation depends directly on the axial position at which the nonlinear interaction occurred. Compared to intensity-based methods which are limited by the depth of focus of the objective, the phase-based method proposed by the present invention is limited only by the wavelengths and is therefore much more accurate, with a sensitivity at the nanometer scale.

In addition, as the nonlinear interactions of interest are instantaneous, they are intrinsically suited for ultrafast measurements. The temporal resolution of the measurement of the position nonlinear interaction thus only depends on the limitations of the EM source wave and the detecting apparatus.

Figure 5:
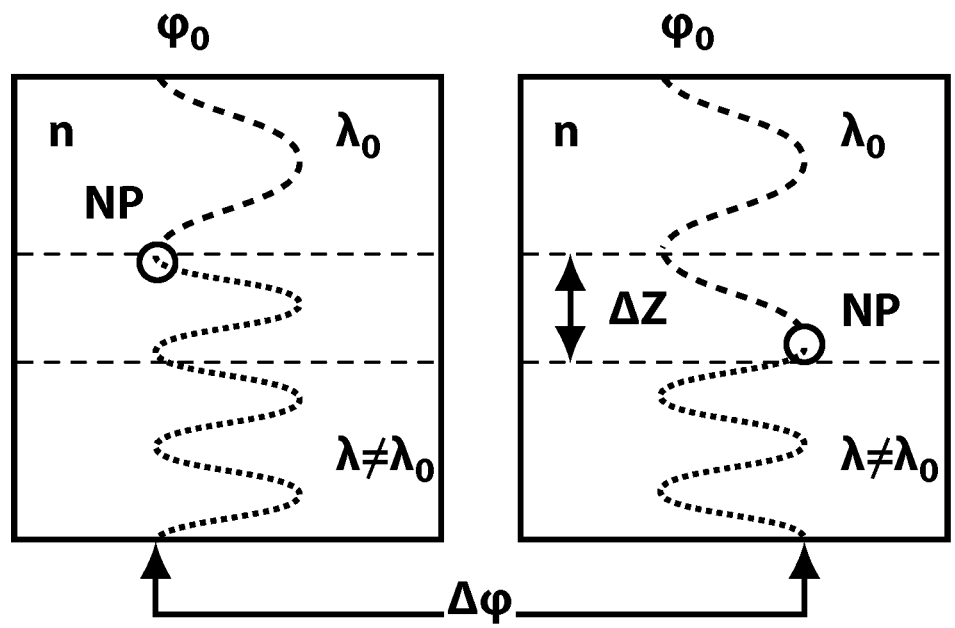
FIG. 5 illustrates how the phase of a nonlinear EM wave changes as the position where the nonlinear interaction occurred, and how this can be applied for, e.g., tracking of nanoparticles.
Figure 6:
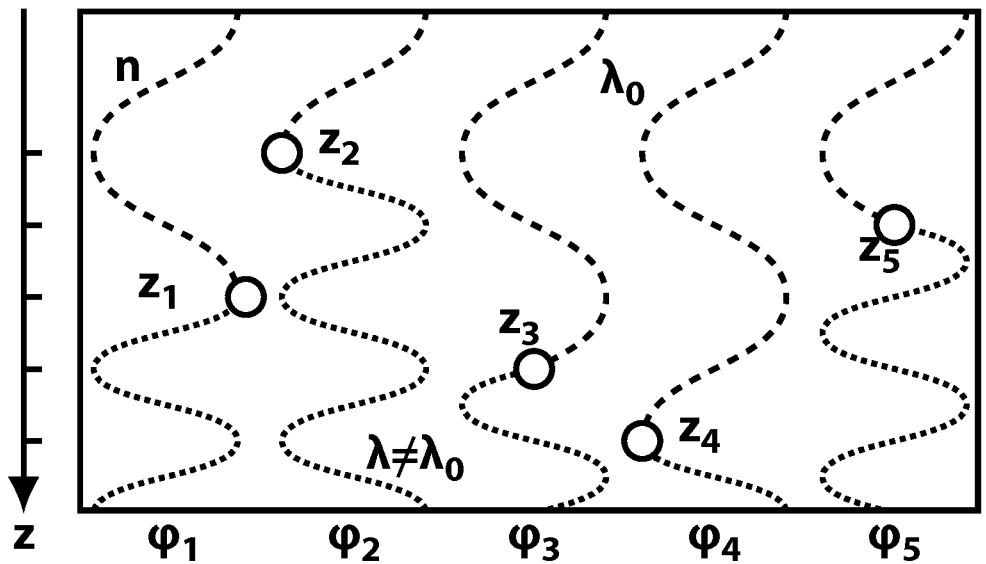
FIG. 6 illustrates how the phase of the nonlinear EM wave can be used for tracking individual particles within a distribution.

By providing a mean to measure the position and time at which occurred a nonlinear interaction, the disclosed invention makes possible 3D-tracking of nonlinear emitters, such as nanoparticles. FIGS. 5 and 6 schematically present an application of the present invention to nanometric 3D-tracking of individual nanoparticles. This application supposes that the nanoparticles have non-zero dielectric polarization response to EM radiation.

In particular, this invention can be used to track movements of nanoparticles along the optical axis. In FIG. 5, a nanoparticle (NP) acts as the nonlinear medium for nonlinear interaction of EM source wave of wavelength $\lambda 0$ that produces a nonlinear EM wave of wavelength $\lambda \neq \lambda 0$. Movements of the NP in the direction of the optical axis, indicated by $\Delta Z$, will result in a phase shift ($\Delta \phi$) that can be detected.

This invention can also be used for nanometer-scale 3D-localization of individual nanoparticles within a distribution and/or a medium. As illustrated in FIG. 6, different particles located at different axial positions can be distinguished on the basis of their phase. Therefore, the present invention can be used to measure the difference of height from one particle to another, as well as the height of each particle with respect to a reference position ($z=0$).

Figure 7:
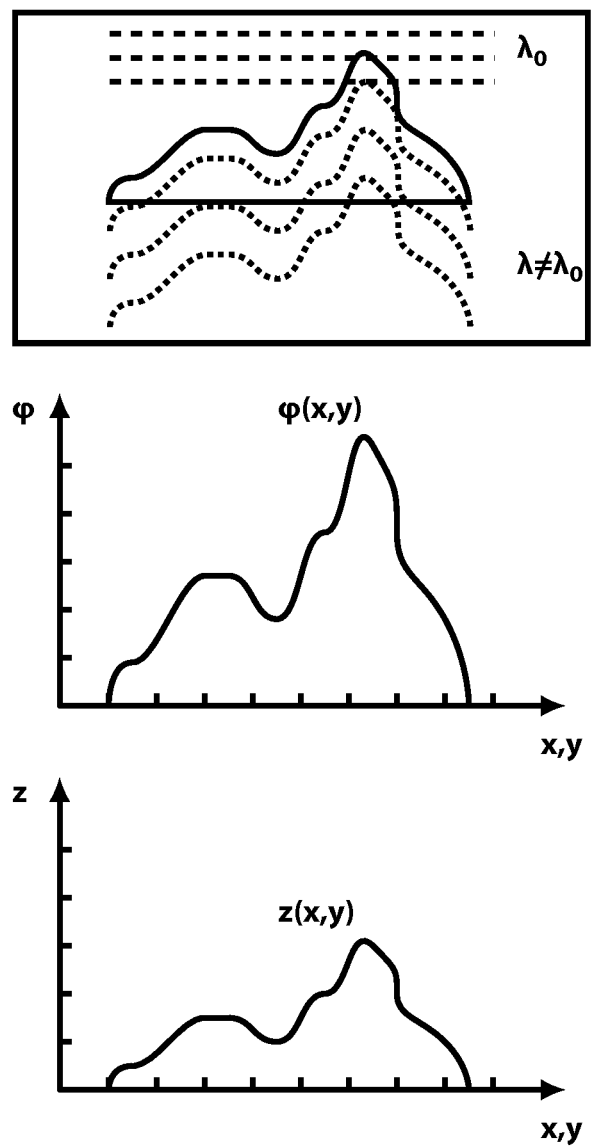
FIG. 7 illustrates how the phase of the nonlinear EM wave can be used for measuring the morphology of a surface.

By extension of FIG. 6, and as presented in FIG. 7, if the non-linear emitted is not a distribution of particles but a continuous, or discontinuous, surface, the present invention can be used to measure the morphology of this surface. For example, the surface can be stained with markers having non-zero dielectric polarization response to EM radiation.

Temporal Monitoring

Movements of particles or surface displacements are not the only temporal processes that can be monitored in three-dimension with the present invention. Indeed, as phase measurements are also highly sensitive to the dielectric properties of the medium, temporal changes of these properties will affect the phase signal of the nonlinear wave. In particular, the present invention can be used to monitor energy or matter fluxes that alter the amplitude and/or the phase of the observed nonlinear EM wave.

As well, functionalized or bioconjugated nonlinear markers can be used to track their target molecule, protein or structure, especially when the targets do not intrinsically exhibit detectable or strong enough nonlinear signals. In addition, changes in the local dielectric properties of the marker and of its surroundings, occurring after the marker has reached its target, can be monitored thanks to the present invention and provide insights on functional dynamics of the target with its environment. This particular feature is of high interest in genomics.

As well, voltage- or current-sensitive nonlinear markers make possible the use of the present invention to monitor electrical activities. This particular feature is of high interest in cell biology, e.g. for neuronal charge-transfer monitoring.

High Sensitivity, High Dynamic Range, and Decoupled OPL Measurements

Apparatus and method according to the present invention can be used for high sensitivity measurements of optical path length difference. Basically, this application relies on the fact that the nonlinear interaction of the EM source, of wavelength $\lambda 0$, with a nonlinear medium produces a nonlinear EM radiation of wavelength $\lambda < \lambda 0$. As a consequence, the nonlinear EM wave is more sensitive to optical path length (OPL) changes.

Apparatus and method according to the present invention can be used for high dynamic range measurements of optical path length difference. Basically, this application relies on the fact that the nonlinear interaction of the EM source, of wavelength $\lambda 0$, with a nonlinear medium produces a nonlinear EM radiation of wavelength $\lambda > \lambda 0$. As a consequence, the nonlinear EM wave is less sensitive to optical path length (OPL) changes and is better suited for measurements of abrupt steps with high aspect ratio.

Apparatus and method according to the present invention can be used for decoupling the contributions to OPL changes caused by the specimen refractive index and its morphology. Basically, this application relies on the fact that the OPL measurement is carried out at two different wavelengths. In particular, the two different wavelengths can be that of the EM source wave ($\lambda 0$) and that of the nonlinear EM wave ($\lambda \neq \lambda 0$). In particular, the two different wavelengths can be that of two different nonlinear EM waves, generated either simultaneously, or successively.

The invention claimed is:

1. Apparatus for retrieving the optical phase and the amplitude of a nonlinear electromagnetic object wave comprising:
   at least one source of electromagnetic radiation probing at least one object, said object comprising at least one element generating a nonlinear interaction with said electromagnetic radiation, said nonlinear interaction resulting in the emission of nonlinear electromagnetic radiation, referred to as the nonlinear object wave,
   at least one detector or detector array for sensing said nonlinear object wave,
   a nonlinear reference wave generated from said source of electromagnetic radiation by a nonlinear interaction, and
   wherein said detector or detector array is configured to sense an interferogram or a hologram resulting from the interference between said nonlinear object wave and said nonlinear reference wave,
   said nonlinear reference wave is generated inside said object, and the apparatus further comprises at least one processing unit connected to said detector or detector array, said processing unit applies a numerical hologram reconstruction method to retrieve the amplitude and the optical phase of said nonlinear object wave, and wherein the nonlinear object wave and the linear reference wave are both produced by harmonic generation of the electromagnetic radiation emitted by the at least one source of electromagnetic radiation, or by sum or difference frequency wave generation of the electromagnetic radiation emitted by the at least one source of electromagnetic radiation, or by multiple-wave mixing through Coherent Anti-Stokes Raman Scattering of the electromagnetic radiation emitted by the at least one source of electromagnetic radiation.

2. Apparatus according to claim 1 wherein said nonlinear object wave is collected by a microscope objective, and wherein said detector array is arranged in order to form an out of focus image of said object.

3. Method using an apparatus according to claim 1 for determining the position at which at least one nonlinear interaction occurred inside said object by using the fact that the phase of a nonlinear wave depends on the position of its emission.

4. Method according to claim 3 for determining the three-dimensional distribution of particles emitting nonlinear radiations within said object.

5. Method according to claim 3 for determining the topography of at least one surface emitting nonlinear radiations within said object.

6. Method according to claim 4 for providing the three-dimensional tomography of structures emitting nonlinear radiations within said object.

7. Method using an apparatus according to claim 1 for monitoring temporal changes of the phase of at least one nonlinear interaction occurring inside said object by using the fact that said apparatus enables real-time phase retrieval.

8. Method according to claim 7 for monitoring movements of structures emitting nonlinear waves within said sample.

9. Method according to claim 7 for monitoring temporal changes of the dielectric properties of structures emitting nonlinear waves within said sample.

10. Method according to claim 7 for monitoring temporal changes of the dielectric properties of matter located adjacent to structures emitting nonlinear waves within said sample.

* * * * *